United States Patent [19]

Ittel et al.

[11] Patent Number: 5,192,730
[45] Date of Patent: Mar. 9, 1993

[54] STABLE SOLUTIONS OF TETRA(HYDROCARBYL)METAL COMPOUNDS AND USE THEREOF FOR CATALYST PREPARATION

[75] Inventors: Steven D. Ittel, Wilmington; Frederick N. Tebbe, Hockessin, both of Del.

[73] Assignee: E. I. Du Pont de Nemours and Company, Wilmington, Del.

[21] Appl. No.: 791,943

[22] Filed: Nov. 13, 1991

[51] Int. Cl.$^5$ .............................................. C08F 4/64
[52] U.S. Cl. ..................................... 502/108; 502/103; 502/117; 502/152
[58] Field of Search ............... 502/103, 108, 117, 152; 556/2

[56] References Cited

U.S. PATENT DOCUMENTS

| | | | |
|---|---|---|---|
| 3,404,096 | 10/1968 | Lamborn | 502/108 |
| 3,840,508 | 10/1974 | Ballard et al. | 260/882 |
| 3,932,307 | 1/1976 | Setterquist | 252/430 |
| 3,950,269 | 4/1976 | Setterquist | 252/430 |
| 3,971,767 | 7/1976 | Setterquist | 526/65 |
| 4,011,383 | 3/1977 | Setterquist | 526/154 |
| 4,017,525 | 4/1977 | Setterquist | 260/429.3 |
| 4,228,263 | 10/1980 | Howard, Jr. et al. | 526/154 |
| 4,304,685 | 12/1981 | Howard, Jr. et al. | 252/430 |
| 4,335,225 | 6/1982 | Collette et al. | 525/240 |
| 4,460,757 | 7/1984 | Sato et al. | 502/108 |

FOREIGN PATENT DOCUMENTS 2001080A 1/1979 United Kingdom.

*Primary Examiner*—Patrick P. Garvin
*Assistant Examiner*—Brent M. Peebles
*Attorney, Agent, or Firm*—Kathleen W. Geiger

[57] ABSTRACT

A process for preparing chemically stable compositions of tetra(hydrocarbyl)metallic compounds in solution, and an improved process for the preparation of active 1-olefin polymerization catalysts.

14 Claims, No Drawings

STABLE SOLUTIONS OF TETRA(HYDROCARBYL)METAL COMPOUNDS AND USE THEREOF FOR CATALYST PREPARATION

FIELD OF THE INVENTION

This invention relates to stabilized solutions of olefin polymerization catalyst precursors, especially solutions of tetra(neophyl)zirconium, and their use in forming active catalysts.

BACKGROUND OF THE INVENTION

U.S. Pat. No. 3,840,508 (Ballard) discloses a process for polymerizing olefinically unsaturated monomers using as an initiator a reaction product of a transition metal complex and a matrix material which has a hydroxylated surface but which is otherwise substantially inert.

U.S. Pat. No. 4,228,263 (Howard) discloses a catalytic process for preparing elastomeric polymers of propylene. The catalyst, which is a reaction product of a metal oxide and an organometallic compound of the formula $(RCH_2)_4M$ wherein M is Zr, Ti, or Hf, and R is aryl, aralkyl, tertiary alkyl, or trialkylsilyl, is prepared in situ in a solvent consisting principally of liquid propylene; the solvent may also contain volatile materials, such as hexane, which are used to introduce the catalyst components. A similar process for preparing elastomeric polypropylene is disclosed in British Specification 2,001,080 (Collette).

U.S. Pat. No. 3,932,307 (Setterquist) discloses a process for polymerizing 1-olefins using a catalyst system based on the reaction product obtained by contacting a solution of tetra(neophyl)zirconium in a hydrocarbon medium, with a hydroxylated oxide of a metal of Group IIa, IIIa, IVa, or IVb of the Periodic Table of the Elements. Fumed alumina, i.e., alumina prepared by burning aluminum chloride in the presence of water vapor, is an exemplified preferred metal oxide and provides an especially active catalyst system. Related catalyst systems and polymerization processes are disclosed in U.S. Pat. Nos. 3,950,269 (Setterquist); 3,971,767 (Setterquist); 4,011,383 (Setterquist); and 4,304,685 (Howard).

In U.S. Pat. No. 4,335,225 (Collette et al.), these types of catalyst systems, which are the reaction product of an organometallic compound with the partially hydrated surface of a metal oxide, are used to polymerize propylene to a novel elastomeric polypropylene. In addition to tetra(neophyl)zirconium, other specified types of organometallic derivatives of Group IVa transition metals, i.e., titanium, zirconium, and hafnium, are described as being suitable catalyst components. The polypropylene polymerization may be carried out by a solution method, in which the propylene is present as a solution in an inert hydrocarbon such as cyclohexane. Alternatively, polymerization may be carried out by a slurry method, wherein the polymerization medium is essentially excess liquid propylene, and only a relatively minor amount of an inert hydrocarbon solvent, from the catalyst suspension, is present. The slurry method is preferred. Hydrogen may be present to control molecular weight. The preferred catalyst in U.S. Pat. No. 4,335,225 is produced from reactions employing tetra(neophyl)zirconium (TNZ), which is disclosed in U.S. Pat. No. 4,017,525 (Setterquist).

Tetra(hydrocarbyl)metallic compounds, such as (TNZ), are usually isolated as solid materials. It is known in this art that these catalyst precursor organometallic compounds in solid form are reasonably stable as such if protected from oxygen and water, and are even more stable if they are also stored below room temperature at about 20° C. or lower. However, if they are not so protected, or if stored in solvents such as n-alkanes, isoalkanes, and aromatics, they are known to decompose with formation of hydrocarbons, colored soluble organometallic compounds, and deeply-colored insoluble organometallic compounds. The composition of the colored species is unknown. Decomposition products of TNZ are tert-butylbenzene and highly-colored (yellow, brown, or black) organometallic compounds. The decomposition products form in detectable amounts within hours or days at room temperature. The formation and precipitation of these organometallic decomposition products leads to deterioration and variability in the activity of the catalysts prepared therefrom.

It would be of great commercial advantage if a solvent, in which these tetra(hydrocarbyl)metallic compounds were stable, were available. This would facilitate the manufacture, storage, and transportation of these compounds, i.e., the solid would not have to be isolated during production, and the solution environment would not have to be kept below 20° C. during containment and storage. It would be even more advantageous if said tetra(hydrocarbyl)metallic compounds in such a stabilizing solvent could be converted to the active catalyst for subsequent use in, e.g., olefin polymerization, without having to re-isolate the solid material and add another hydrocarbon solvent.

The present invention provides a process to achieve a chemically stable composition of organometallic catalyst precursor compounds in solution form. Costs of refrigeration in storing and transporting the catalyst precursor can then be reduced or eliminated; improved convenience in handling is achieved; and uniformity in the activity of the resulting activated catalyst can be realized. The present invention also provides a composition comprising organometallic catalyst precursors in solution form, which can be used directly to make activated catalysts, thereby providing a significant improvement in the catalyst preparation process.

Applicants have found that the compositions of the present invention are stable for much longer periods of time than those in the solvents used previously; and have further found that the compositions of the present invention can be added directly to the catalyst preparation process, i.e., the olefins of the composition do not inhibit formation of an activated catalyst. These results were unexpected in light of the prior art, and the fact that the activated catalysts derived from the compositions of this invention are normally used for olefin polymerization. Even more unexpected was the fact that the activated olefin polymerization catalysts could be formed in the presence of the olefins of the present invention without any loss in catalytic activity.

SUMMARY OF THE INVENTION

This invention provides a process for chemically stabilizing a tetra(hydrocarbyl)metallic compound in solution, comprising:

dissolving a tetra(hydrocarbyl)metallic compound of the formula $(RCH_2)_4M$, wherein M is an element selected from the group consisting of Ti, Zr and Hf, and R is a hydrocarbyl group wherein the carbon atom located $\beta$ to M is devoid of hydrogen;

in a solution containing one or more olefins of the formula $R^1R^2C=CR^3R^4$, wherein each of $R^1$ and $R^2$, independently, is an aliphatic group containing 1-10 carbon atoms, or an aralkyl group containing 7-10 carbon atoms; and each of $R^3$ and $R^4$, independently, is H, an aliphatic group containing 1-10 carbon atoms, or an aralkyl group containing 7-10 carbon atoms; or wherein $R^1$ together with either $R^2$, $R^3$ or $R^4$ forms a carbocyclic ring containing 5-12 carbon atoms;

wherein the final concentration of said tetra(hydrocarbyl)metallic compound is at least about 0.01 mol/L.

This invention further provides a composition comprising a chemically stable solution of:

a tetra(hydrocarbyl)metallic compound of formula $(RCH_2)_4M$, wherein M is an element selected from the group consisting of Ti, Zr and Hf, and R is a hydrocarbyl group wherein the carbon atom located $\beta$ to M is devoid of hydrogen, in an olefin of the formula $R^1R^2C=CR^3R^4$, wherein each of $R^1$ and $R^2$, independently, is an aliphatic group containing 1-10 carbon atoms, or an aralkyl group containing 7-10 carbon atoms; and each of $R^3$ and $R^4$, independently, is H, an aliphatic group containing 1-10 carbon atoms, or an aralkyl group containing 7-10 carbon atoms; or wherein $R^1$ together with either $R^2$, $R^3$ or $R^4$ forms a carbocyclic ring containing 5-12 carbon atoms;

wherein the final concentration of said tetra(hydrocarbyl)metallic compound in solution is at least about 0.01 mol/L.

This invention further provides an improvement in the process for the preparation of 1-olefin polymerization catalysts, which is described in U.S. Pat. No. 4,304,685 and U.S. Pat. No. 3,932,307. The process comprises reacting a porous alumina with an organometallic compound of the formula $(RCH_2)_4M$, wherein M is Ti, Zr or Hf, and R is a hydrocarbyl wherein the carbon atom located $\beta$ to M is devoid of hydrogen; the improvement comprises carrying out said reaction by addition of the organometallic compound in a solution of olefin of the formula $R^1R^2C=CR^3R^4$, wherein each of $R^1$ and $R^2$, independently, is an aliphatic group containing 1-10 carbon atoms, or an aralkyl group containing 7-10 carbon atoms; each of $R^3$ and $R^4$, independently, is H, an aliphatic group containing 1-10 carbon atoms, or an aralkyl group containing 7-10 carbon atoms; or wherein $R^1$, together with either $R^2$, $R^3$ or $R^4$ forms a carbocyclic ring containing 5-12 carbon atoms; wherein the final concentration of said tetra(hydrocarbyl)metallic compound in solution is at least about 0.01 mol/L.

DETAILED DESCRIPTION OF THE INVENTION

The process of the present invention is useful in that it provides tetra(hydrocarbyl)metallic compounds in the form of stable solutions, which provide convenience and cost-effectiveness in long-term storage, transportation and handling. The compositions of the invention are useful as catalyst precursors, which can be added directly in the catalyst preparation reaction to prepare catalysts for the polymerization of ethylene to polyethylene, of propylene to elastomeric polypropylene, as well as of other 1-olefins, such as 1-pentene, 1-octene, and 1-dodecene, to the respective polyolefins. The instant invention provides further utility in that it improves the process for preparation of a 1-olefin polymerization catalyst.

The organometallic compounds used in this invention are tetra(hydrocarbyl)metallic compounds of formula, $(RCH_2)_4M$, wherein M is an element selected from among the group consisting of Ti, Zr and Hf, and R is a hydrocarbyl group wherein the carbon atom located $\beta$ to M is devoid of hydrogen. More specifically, R may be an aryl, aralkyl or tertiary alkyl, e.g., trialkylmethyl. Examples of $RCH_2$— include, but are not limited to neophyl, neopentyl, and benzyl. Representative organometallic compounds include, but are not limited to, tetra(neophyl)zirconium, -titanium, or -hafnium; tetra(neopentyl)zirconium, -titanium, or -hafnium; and tetra(benzyl)zirconium, -titanium, or -hafnium.

The tetra(hydrocarbyl)metallic compounds of this invention can be made by procedures well known in the art, e.g., the syntheses of tetra(benzyl)titanium and tetra(benzyl)zirconium are given in Zucchini, U., et al., J. Organometal. Chem., 26, 357-372, 1971; and the synthesis of tetra(neophyl)zirconium is given in U.S. Pat. No. 4,017,525, U.S. Pat. No. 3,932,307 and U.S. Pat. No. 3,950,269, which are hereby incorporated by reference.

The stability of tetra(hydrocarbyl)metallic compounds in solution is achieved by adding a solvent containing from about 5 to 100% by weight of an olefin of the formula, $R^1R^2C=CR^3R^4$, wherein each of $R^1$ and $R^2$, independently, is an aliphatic group containing 1-10 carbon atoms, or an arylaliphatic group containing 7-10 carbon atoms; each $R^3$ and $R^4$, independently, is H, an aliphatic group containing 1-10 carbon atoms, or an arylaliphatic group containing 7-10 carbon atoms. The group $R^1$, taken together with either $R^2$, $R^3$, or $R^4$, can alternatively form a carbocyclic ring containing 5-12 carbon atoms. Preferred examples of the olefin include methylenecyclohexane and 2,3-dimethyl-2-butene. The most preferred example is 2-methylpropene(isobutylene), because of its relative low cost and low boiling point, which facilitates removal before polymerization. The rest of the solvent is composed of non-interfering aliphatic or aromatic hydrocarbons. Interfering hydrocarbons are ones that react with the tetra(hydrocarbyl)metallic compound. For instance, 1-olefins, such as 1-pentene or 1-octene, slowly oligomerize or polymerize in the presence of tetra(hydrocarbyl)metallic compounds. Diolefins, such as isoprene, also polymerize in the presence of tetra(hydrocarbyl)metallic compound, yielding viscous solutions. These reactions may be the result of adventitious moisture, but nonetheless, are virtually impossible to avoid. Examples of non-interfering hydrocarbons include, but are not limited to: hexane, cyclohexane, benzene, toluene, and mesitylene.

The final concentration of the tetra(hydrocarbyl)metallic compound in the solvent is at least 0.01 mol/L, and preferably the solvent is saturated in the tetra(hydrocarbyl)metallic compound. In order to expedite transportation and storage, the saturated solution may also contain excess solid tetra(hydrocarbyl)metallic compound.

In order to form the active catalyst, the catalyst precursor composition solution comprising the tetra(hydrocarbyl)metallic compound and the solvent, is contacted with a suitable inorganic support or filler compound, which has been specially activated. Alternatively, the olefin solvent may be removed, e.g., by evaporation or distillation, and another solvent added before reaction of the tetra(hydrocarbyl)metallic compound with the support or filler. Details of the process including preferred conditions for producing a 1-olefin polymerization catalyst are provided in U.S. Pat. No. 3,932,307, U.S. Pat. No. 4,335,225 and U.S. Pat. No. 4,187,210, which are hereby incorporated by reference. The process is particularly described, for example, in Claim 4 of U.S. Pat. No. 3,932,307, wherein the improvement provided by the instant invention would occur at step d of Claim 4. In this step, the "solution of tetra(neophyl)zirconium in a anhydrous liquid hydrocarbon" is replaced with a solution comprised of the composition of the instant invention. This composition can be added directly to the activated alumina in the chemically stable form in which it had previously been stored, thus providing a uniform, cost-effective and convenient method of producing activated polymerization catalysts.

The 1-olefins that can be homopolymerized and/or copolymerized by means of these catalysts include, in particular, ethylene, propylene, 1-butene, 1-pentene, 1-hexene, 1-heptene, 1-octene, 1-nonene, 1-decene, 1,4-hexadiene, and other dienes having at least one terminal olefinic group. Homopolymers and copolymers that can be and/or have been prepared by the process of this invention, some of which preparations are described in the examples hereinafter, include ethylene and propylene homopolymers as well as ethylene-propylene and propylene-dodecene copolymers.

EXAMPLE 1

A solution of 0.2 g TNZ in 3.0 mL methylenecyclohexane was sealed in a glass tube. A comparison sample, consisting of a solution of 0.2 g TNZ in 3.0 mL cyclohexane, was also sealed in a glass tube. The volumes of the tubes were ca. 4 mL. The tubes were heated 1 h at 52° C. After heating, the cyclohexane solution was more deeply colored than the methylenecyclohexane solution, showing that decomposition in cyclohexane was more extensive than in methylenecyclohexane.

EXAMPLE 2

A solution of 0.1 g TNZ in 76 μL methylenecyclohexane and about 0.6 mL of toluene-$d_8$ was sealed in an NMR tube. A comparison sample consisted of a solution of 0.1 g TNZ in about 0.6 mL of toluene-$d_8$, also sealed in an NMR tube. After the tubes were heated 1.5 h at 50° C., the solution containing methylenecyclohexane was colorless, showing that little or no decomposition had occurred. The solution in which methylenecyclohexane was absent was pale tan, showing that a small amount of decomposition had occurred. After 16 h at 50° C., the color of the solution containing methylenecyclohexane was a very pale tan, and tert-butylbenzene was not detected in the proton NMR spectrum, showing that little or no decomposition had occurred. The solution in which methylenecyclohexane was absent was dark brown and contained tert-butylbenzene, showing that a significant amount of decomposition had occurred.

EXAMPLE 3

The effects of three olefins, cyclohexene, methylenecyclohexane, and 1-hexene, on formation of solids in cyclohexane solutions of tetra(neophyl)zirconium (TNZ) were examined. Cyclohexane solutions 0.2M in TNZ and 2M in olefin were contained in sealed tubes (total volume of solution ca. 0.5 mL) and heated 6 days at 53° C. The quantity of solid formed in the solution containing cyclohexene was large compared to quantities formed in the solutions containing methylenecyclohexane and 1-hexene.

EXAMPLE 4

Isobutene, at a pressure of 23 psi (158.6 kPa), was contained in a pressure tube over a solution of 1 g of TNZ in 4 mL of toluene. A control, containing 1 g of TNZ in 5 mL of toluene, was also run simultaneously. The solutions were kept at 50° C. for 72 h; black solids did not form in the tube containing the isobutene during this period, compared to the control without any olefin, which formed black solids.

EXAMPLE 5

Propylene (1.2 mmol) was contained in a pressure tube over a solution of 0.07 g (0.11 mmol) of TNZ in 1 mL of toluene. The solution was heated to 50° C.; after 16 h, the clear, light-tan solution turned to light-brown and contained white solid, which was assumed to be polypropylene. The $^1$H NMR spectrum of the soluble material corresponded to TNZ. The conclusion was that propylene inhibited conversion of TNZ to insoluble solid, but a portion of the olefin polymerized.

EXAMPLE 6

A mixture of 0.1 g TNZ, 0.16 mmol of ethylene, and ca. 0.6 mL toluene-$d_8$ was sealed in an NMR tube. The mixture was heated to 50° C. for 16 h. Polymeric material and a deeply colored organometallic mixture formed. Neither TNZ nor ethylene could be detected by $^1$H NMR.

EXAMPLE 7

The stability of 0.25 g samples of TNZ at room temperature in 2.0 mL of hexane, octene, and isoprene (2-methyl-1,3-butadiene) were compared. The hexane solution blackened within 48 h. The octene solution was brown-gold within 48 h and was dark brown within 6 days; the solution had thickened, indicating polymerization. The isoprene sample was yellow brown within 48 h and polymer formation was evident. After 6 days, the solution had taken on an additional reddish tint and polymer had formed.

These examples serve to indicate that α-olefins will stabilize TNZ, but that polymer formation, which is undesirable, accompanies the stabilization. Isoprene, a conjugated diene, also inhibits formation of black color but with polymer formation.

EXAMPLE 8

The stability of 0.25 g samples of TNZ at room temperature in 2.0 mL toluene containing varying portions of 2-methyl-1-pentene (or 1-methyl-1-propylethylene) were compared. The solution in neat toluene turned black within 48 h. A solution with about 5% by volume added 2-methyl-1-pentene blackened somewhat less quickly. A solution containing about 13% added 2-methyl-1-pentene was still light after 48 h, was brown after 6 days, and was black after 28 days.

This example indicates that neat olefin need not be used to achieve the desired stabilization. Increasing concentrations of the stabilizing olefin provide increased protection.

EXAMPLE 9

The stability of 0.25 g samples of TNZ at room temperature in hexane and methylenecyclohexane were compared. The solution of TNZ in 2.0 mL neat hexane turned black within 48 h. A similar solution in 2.0 mL neat methylenecyclohexane was yellow brown after 48 h, very dark brown after 6 days, and black after 28 days.

This example illustrates that the substituents on the olefin may be joined in a carbocyclic ring and still provide protection.

EXAMPLE 10

The stability of samples of TNZ at room temperature in hexane, isobutene (1,1-dimethylethylene), or 2,3-dimethyl-2-butene (1,1,2,2-tetramethylethylene, TME) were compared. The solution in neat hexane turned black within 48 h. Similar solutions in isobutene and TME were still very pale yellow after 48 h. After 6 days the solution in isobutene was pale yellow-brown and the solution in TME was still pale yellow. After 28 days, the isobutene solution was brown-black and the TME solution was tan. This example illustrates that increasing the number of alkyl substituents on the olefin provides additional protection.

EXAMPLE 11

Tetra(benzyl)zirconium (TBZ) (0.25 g) was dissolved in toluene (6.55 g) at room temperature. Half of the resulting solution (3.4 g) was placed in a quartz Fisher Porter tube. Isobutene (1.6 g) was condensed into the tube giving a solution of TBZ in toluene/isobutene. The solution in pure toluene turned dark brown within an hour. The solution in toluene/isobutene remained bright yellow. In 24 h, the toluene solution was black and the toluene/isobutene solution was orange-brown. After a week, the toluene/isobutene solution was still orange-brown.

The example serves to indicate that the alkyl substituents on the metal center of TBZ may include aromatic groups bound directly to the alpha-carbon atom.

Standard Synthesis of Elastomeric Polypropylene

Examples 12-15 below were included to demonstrate use of the composition of the invention to form activated catalyst, which successfully polymerized polypropylene. A description of the catalyst preparation and polymerization materials used in these examples is provided below. Further details of this process are provided in U.S. Pat. No. 4,335,225, which is hereby incorporated by reference.

Degussa fumed alumina-C was dried under a flow of nitrogen at 400°-900° C. to achieve a surface hydroxyl count of 0.6-1.2 mmol per gram of $Al_2O_3$. In the inert atmosphere (nitrogen or argon) of a Vacuum Atmospheres drybox, the alumina (1-4 g) was suspended in 20-40 g hexane. A solution of 0.13-1.0 g tetra(neophyl)zirconium in 8-32 g hexane was added to the alumina suspension. The viscosity of the suspension rapidly decreased, with tert-butylbenzene being liberated as the zirconium was fixed to the alumina surface. The suspension was stirred for ca. 10-60 sec using a biohomogenizer and then transferred to a polyethylene squeeze-bottle, which was sealed with a Luer-lock valve. The bottle was pressurized with nitrogen to ca. 0.05-0.1 MPa and sealed in a glass jar for transportation to the autoclave.

The 1 gal (3.785 L) autoclave was equipped with a mechanical stirrer, temperature controller, water-cooled walls, blow-case, and an inlet for propylene. The autoclave was sealed, evacuated, and heated to a temperature greater than 150° C. to remove any residual moisture and check for leaks. It was then cooled to room temperature and charged with 800-1000 g propylene (standard polymer grade, passed through a bed of activated BASF $R^3$-11 catalyst for oxygen removal and then through a bed of dried 3A molecular sieve for water removal). The contents of the reactor were brought to a temperature ca. 20° below the desired polymerization temperature of 40°-70° C. The blow-case was thoroughly purged with nitrogen. The catalyst in the squeeze bottle was introduced into the blow-case via a Luer-lock cannula against the purge of nitrogen. The vent was sealed and the pressure of the blow-case was raised above the autogenous pressure of the autoclave. The catalyst was introduced into the autoclave under nitrogen pressure. A mild exotherm raised the temperature of the autoclave by ca. 20° C.; the temperature was regulated at the desired polymerization temperature. Polymerization reactions were run 30 min to 4 h, depending on conditions (primarily temperature). When the polymerization was complete, the propylene was vented, and the autoclave opened to remove the polymer. The temperature was maintained at ca. 60°±10° C. during the venting process to minimize solubility of the polymer in propylene, and to prevent polymer particles from becoming highly agglomerated. The isolated polymer was washed several times with methanol, acetone, or other polar solvent (this was most easily done in an air-driven blender), and dried under vacuum or nitrogen flush to remove the washing solvent and residual propylene. If desired, appropriate stabilizers and antioxidants were added during washing process. Yields were 250-500 g (i.e., 1-2 kg polypropylene per gram TNZ).

EXAMPLE 12

A solution of 0.25 g TNZ in 2 mL neat methylenecyclohexane was allowed to stand overnight at room temperature. The methylenecyclohexane was removed under vacuum; no change was apparent in the TNZ. The TNZ was dissolved in 16 g hexane and reacted with 2.0 g dried Degussa alumina (surface hydroxy content 0.75 mmol per gram $Al_2O_3$) slurried in 20 g hexane. The resulting catalyst was used to polymerize propylene (see Standard Synthesis of Elastomeric Polypropylene) to yield 328 g of elastomeric polypropylene. Two control runs using TNZ that had not been exposed to methylenecyclohexane yielded 328 g and 441 g, respectively, of polymer.

This illustrates that exposure of the tetra(hydrocarbyl)metallic compound to stabilizing olefins or storage in the stabilized solution has no effect on the tetra(hydrocarbyl)metallic compound when it is used in subsequent preparation of olefin polymerization catalysts.

EXAMPLE 13

A solution of 5 g TNZ in 50 mL neat isobutene was contained in a stainless steel Hoke cylinder. After three weeks at room temperature, a small portion of the light tan mixture was discharged from the cylinder. The isobutene was allowed to evaporate, yielding solid ranging from tan to brown. A portion of the solid TNZ (0.25 g) was taken up in 20 g hexane and reacted with 2.0 g dried Degussa alumina (surface hydroxy content of 0.75 mmol per gram $Al_2O_3$) slurried in 20 g hexane. The resulting catalyst was used to polymerize propylene (see Standard Synthesis of Elastomeric Polypropylene) to yield 148 g of elastomeric polypropylene.

EXAMPLE 14

A solution of 0.250 g TNZ in 5 μL neat methylenecyclohexane was reacted with 2.0 g dried Degussa alumina (surface hydroxy content of 0.75 mmol per gram $Al_2O_3$) slurried in 20 g hexane. The mixture was gravity filtered through a glass frit to remove most of the methylenecyclohexane from the solid catalyst. The resulting solid was resuspended in 36 g hexane and was used to polymerize propylene (see Standard Synthesis of Elastomeric Polypropylene) to yield 128 g of elastomeric polypropylene.

EXAMPLE 15

A solution of 0.250 g TNZ in 5 mL neat methylenecyclohexane was reacted with 2.0 g dried Degussa alumina (surface hydroxy content of 0.75 mmol per gram $Al_2O_3$) slurried in 20 g hexane. The resulting catalyst was used under normal propylene polymerization conditions (see Standard Synthesis of Elastomeric Polypropylene), but yielded no elastomeric polypropylene. This experiment demonstrated that isoolefins transferred into the α-olefin polymerization reaction will inhibit polymerization.

What is claimed is:

1. A composition comprising a chemically stable solution of:
   a tetra(hydrocarbyl)metallic compound of the formula, $(RCH_2)_4M$, wherein M is an element selected from the group consisting of Ti, Zr and Hf, and R is a hydrocarbyl group wherein the carbon atom located β to M is devoid of hydrogen,
   in an olefin of the formula, $R^1R^2C=CR^3R^4$, wherein each of $R^1$ and $R^2$, independently, is an aliphatic group containing 1–10 carbon atoms, or an aralkyl group containing 7–10 carbon atoms; and each of $R^3$ and $R^4$, independently, is H, an aliphatic group containing 1–10 carbon atoms, or an aralkyl group containing 7–10 carbon atoms; or wherein $R^1$, taken together with either $R^2$, $R^3$, or $R^4$ forms a carbocyclic ring containing 5–12 carbon atoms;
   wherein the final concentration of said tetra(hydrocarbyl)metallic compound in solution is at least about 0.01 mol/L.

2. The composition of claim 1 wherein one or more non-interfering hydrocarbon solvents are present in addition to the olefin at a total concentration of not greater than 20 times by weight of that of the olefin.

3. The composition of claim 1 wherein M is Zr.

4. The composition of claim 1 wherein R is 2-phenylpropyl or phenyl.

5. The composition of claim 1 wherein the olefin is isobutylene.

6. The composition of claim 1 further comprising solid tetra(hydrocarbyl)metallic compound.

7. The composition of claim 1 wherein the tetra(hydrocarbyl)metallic compound is tetra(neophyl)zirconium.

8. The composition of claim 1 wherein said olefin is isobutylene and said tetra(hydrocarbyl)metallic compound is tetra(neophyl)zirconium.

9. A process for chemically stabilizing a tetra(hydrocarbyl)metallic compound comprising:
   dissolving a tetra(hydrocarbyl)metallic compound of the formula $(RCH_2)_4M$, wherein M is an element selected from the group consisting of Ti, Zr and Hf, and R is a hydrocarbyl group wherein the carbon atom located β to M is devoid of hydrogen
   in a solution containing one or more olefins of the formula $R^1R^2C=CR^3R^4$, wherein each of $R^1$ and $R^2$, independently, is an aliphatic group containing 1–10 carbon atoms, or an aralkyl group containing 7–10 carbon atoms; and each of $R^3$ and $R^4$, independently, is H, an aliphatic group containing 1–10 carbon atoms, or an aralkyl group containing 7–10 carbon atoms; or wherein $R^1$, taken together With either $R^2$, $R^3$ or $R^4$, forms a carbocyclic ring containing 5–12 carbon atoms;
   wherein the final concentration of said tetra(hydrocarbyl)metallic compound is at least about 0.01 mol/L.

10. The process of claim 9, further comprising adding other non-interfering hydrocarbon solvents, in addition to said olefin, at a concentration of not greater than 20 times by weight of that of said olefin.

11. The process of claim 9, wherein the tetra(hydrocarbyl)metallic compound is tetra(neophyl)zirconium, and the olefin is isobutylene.

12. In a process for the preparation of a 1-olefin polymerization catalyst in which a porous alumina is reacted with an organometallic compound of the formula $(RCH_2)_4M$, wherein M is Ti, Zr or Hf and R is a hydrocarbyl wherein the carbon atom located β to M is devoid of hydrogen,
   the improvement which comprises carrying out said reaction by addition of the organometallic compound in one or more olefins of the formula $R^1R^2C=CR^3R^4$, wherein each of $R^1$ and $R^2$, independently, is an aliphatic group containing 1–10 carbon atoms, or an aralkyl group containing 7–10 carbon atoms; each of $R^3$ and $R^4$, independently, is H, an aliphatic group containing 1–10 carbon atoms, or an aralkyl group containing 7–10 carbon atoms; or wherein $R^1$, taken together with either $R^2$, $R^3$, or $R^4$, forms a carbocyclic ring containing 5–12 carbon atoms; wherein the final concentration of said tetra(hydrocarbyl)metallic compound in solution is at least about 0.01 mol/L.

13. The process of claim 12, further comprising the additional step of removing said olefin.

14. The process of claim 12, wherein the tetra(hydrocarbyl)metallic compound is tetra(neophyl)zirconium, and the olefin is isobutylene.

* * * * *